Figure 1:
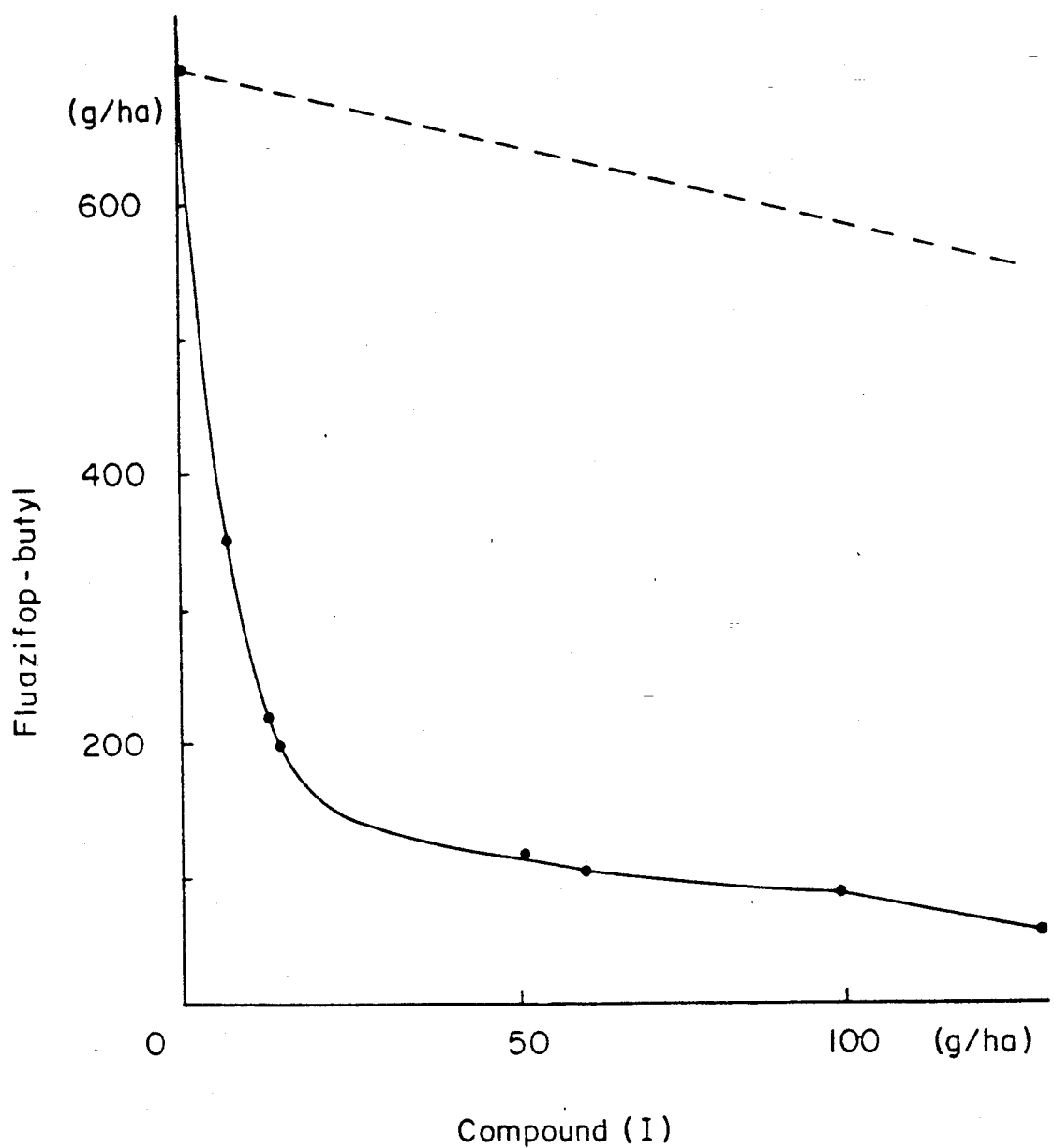

United States Patent [19]

Yoshida et al.

[11] Patent Number: 5,098,463
[45] Date of Patent: Mar. 24, 1992

[54] HERBICIDAL COMPOSITION

[75] Inventors: Ryo Yoshida, Misawa; Yoshihiro Mano, Shiga; Hideyuki Shibata, Takarazuka, all of Japan

[73] Assignee: Sumitomo Chemical Company, Ltd., Osaka, Japan

[21] Appl. No.: 574,117

[22] Filed: Aug. 29, 1990

Related U.S. Application Data

[62] Division of Ser. No. 404,609, Sept. 8, 1989, Pat. 4,975,114.

[51] Int. Cl.$^5$ .................. A01N 43/38; A01N 43/60
[52] U.S. Cl. .................................. 71/92; 71/96
[58] Field of Search ........................ 71/88, 92, 96

[56] References Cited

U.S. PATENT DOCUMENTS

4,640,707  2/1987  Nagano et al. ..................... 71/96

OTHER PUBLICATIONS

The Agrochemicals Handbook, 2nd Ed., The Royal Society of Chemistry, 1987, Ed. Hartley and Kidd.

Primary Examiner—Richard L. Raymond
Assistant Examiner—B. Bembenick
Attorney, Agent, or Firm—Birch, Stewart, Kolasch & Birch

[57] ABSTRACT

A herbicidal composition which comprises as an active ingredient a herbicidally effective amount of the combination of (a) 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione and (b) a compound of the formula:

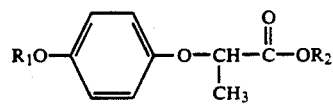

wherein $R_1$ is any one of the formulas:

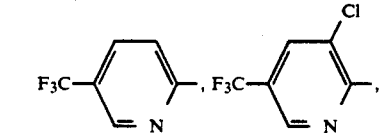

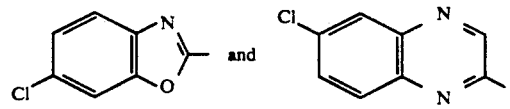

wherein $R_2$ is a $C_1$–$C_4$ alkyl group, and an inert carrier or diluent. The composition shows a synergistic herbicidal potency.

2 Claims, 2 Drawing Sheets

HERBICIDAL COMPOSITION

This application is a divisional of copending application Ser. No. 07/404,609 filed on Sept. 8, 1989 now U.S. Pat. No. 4,975,114.

The present invention relates to a herbicidal composition. More particularly, it relates to a herbicidal composition comprising as the active ingredients (a) 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione (hereinafter referred to as "Compound (I)") of the formula:

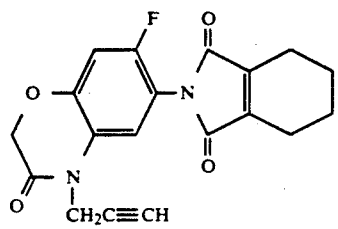

and (b) a compound of the formula:

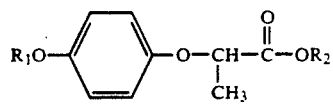

wherein $R_1$ is any one of the formulas:

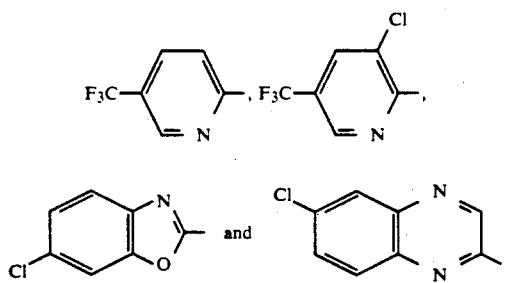

wherein $R_2$ is a $C_1$-$C_4$ alkyl group (hereinafter referred to as "Compound (II)").

A great number of chemicals having a herbicidal activity have been used to exterminate or control the undesired vegetation of weeds in agricultural and non-agricultural fields. Since, however, weeds are diversified in kinds and their growth extends over a long period of time, the herbicidal effects of conventional herbicidal agents are quite restricted in general. Consequently, the appearance of any herbicidal agent which exerts a strong herbicidal activity against a wide variety of weeds without any material phytotoxicity to crop plants has been highly demanded.

No-till cultivation has recently been developed for saving labor, extending the cultivation period, preventing a soil decrease, etc. Because of this reason, there is a demand for herbicides which exert a distinct herbicidal activity in foliar treatment, maintain a prolonged herbicidal efficacy in soil treatment and show a prominent selectivity to crop plants.

As the result of an extensive study, it has now been found that the associated use of Compound (I) and Compound (II) as the active ingredients produces a highly enhanced herbicidal activity against a wide variety of weeds in agricultural and non-agricultural fields. In comparison with the sole use of each of the active ingredients, enhancement of the herbicidal potency on such associated use is remarkable so that the active ingredients may be applied in a smaller dosages. Further, the weed-control spectrum is greatly enlarged. Thus, a clear and definite synergistic effect is observed in said associated use. They can be used with high safety for no-till cultivation of crop plants such as soybean and peanut crops.

The herbicidal composition of the invention can exterminate or control a variety of weeds, of which examples are broad-leaved weeds such as wild buckwheat (*Polygonum convolvulus*), pale smartweed (*Polygonum lapathifolium*), curly dock (*Rumex crispus*), common purslane (*Portulaca oleracea*), common chickweed (*Stellaria media*), common lambsquarters (*Chenopodium album*), slender amaranth (*Amaranthus gracilis*), redroot pigweed (*Amaranthus retroflexus*), radish (*Raphanus sativus*), wild mustard (*Sinapis arvensis*), shepherdspurse (*Capsella bursa-pastoris*), hemp sesbania (*Sesbania exaltata*), sicklepod (*Cassia obtusifolia*), velvetleaf (*Abutilon theophrasti*), prickly sida (*Sida spinosa*), field pancy (*Viola arvensis*), catchweed bedstraw (*Galium aparine*), ivyleaf morningglory (*Ipomoea hederacea*), tall morningglory (*Ipomoea purpurea*), field bindweed (*Convolvulus arvensis*), purple deadnettle (*Lamium purpureum*), henbit (*Lamium amplexicaure*), jimsonweed (*Datura stramonium*), black night-shade (*Solanum nigrum*), persian speedwell (*Veronica persica*), common cocklebur (*Xanthium strumarium*), common sunflower (*Helianthus annuus*), scentless chamomile (*Matricaria perforata*), corn marigold (*Chrysanthemum segetum*) and Japanese mugwort (*Artemisia princeps*); Gramineae weeds such as Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), meadow foxtail (*Alopecurus pratensis*), blackgrass (*Alopecurus myosuroides*), water foxtail (*Alopeculus geniculatus*), oats (*Avena sativa*), wild oats (*Avena fatua*), johnsongrass (*Sorghum halepense*), quackgrass (*Agropyron repens*), downy brome (*Bromus tectorum*) and bermudagrass (*Cynodon dactylon*); Commelinaceae weeds such as asiatic dayflower (*Commelina communis*); Cyperaceae weeds such as rice flatsedge (*Cyperus iria*) and purple nutsedge (*Cyperus rotundus*), etc.

Compound (I) is known to exert a herbicidal activity (U.S. Pat. No. 4,640,707). Compound (II) is also known as a herbicide (The Pesticide Manual, Ed. by The British Crop Protection Council, Vol. 8, pages 379, 404 and 453; Farm Chemicals Handbook 1986, C225). Some examples of Compound (II) are shown in Table 1 below.

TABLE 1

| Chemical structure | Remarks |
|---|---|
| 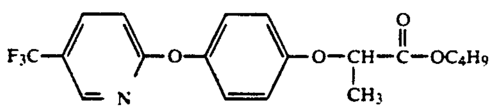 | Fluazifopbutyl |
| 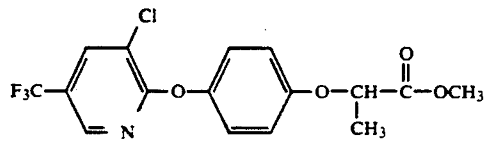 | Haloxyfopmethyl |
| 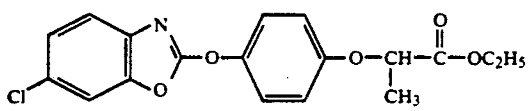 | Fenoxapropethyl |
| 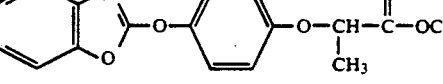 | Quizalofopethyl |

However, the associated use of Compound (I) and Compound (II) has never been attempted, and the production of any synergistic effect on such associated use has never been expected.

The proportion of Compound (I) and Compound (II) as the active ingredients in the composition of the invention may vary within a considerably broad range. Generally, however, Compound (II) may be used in an amount of about 0.4 to 50 parts by weight, preferably of about 0.4 to 20 parts by weight, to one part by weight of Compound (I).

In addition to the above active ingredients, the composition may contain a solid or liquid carrier or diluent. Any surface active or auxiliary agent may be also incorporated therein. Thus, the composition may be formulated in any conventional preparation form such as wettable powder or suspension. The total content of the active ingredients in the composition may be from about 1 to 90 % by weight, preferably from about 2 to 80% by weight.

As the solid carrier or diluent, there may be used kaolin clay, attapulgite clay, bentonite, terra alba, pyrophyllite, talc, diatomaceous earth, calcite, walnut-shell powder, urea, ammonium sulfate, synthetic hydrated silica, etc. Examples of the liquid carrier or diluent are water, etc.

The surface active agent used for dispersion or spreading may be any of the anionic and nonionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymers, sorbitan fatty acid esters, polyoxyethylene sorbitan fatty acid esters, etc. Examples of the auxiliary agent include ligninsulfonates, sodium alginate, polyvinyl alcohol, gum arabic, CMC (carboxymethyl cellulose), PAP (isopropyl acid phosphate), etc.

Practical embodiments for preparation of the composition are illustratively shown in the following Formulation Examples wherein part(s) are by weight.

FORMULATION EXAMPLE 1

Fifteen parts of Compound (I), 30 parts of fluazifop-butyl, 3 parts of calcium ligninsulfonate, 2 parts of sodium laurylsulfate and 50 parts of synthetic hydrated silica are mixed well while being powdered to obtain a wettable powder.

FORMULATION EXAMPLE 2

One part of Compound (I), 1 part of quizalofop-ethyl, 0.5 part of polyoxyethylene sorbitan monooleate, 0.5 part of CMC and 97 parts of water are mixed and pulverized until the particle size becomes less than 5 microns to obtain a suspension.

FORMULATION EXAMPLE 3

7.27 parts of Compound (I), 72.73 parts of fluazifop-butyl, 3 parts of calcium ligninsulfonate, 2 parts of sodium laurylsulfate and 15 parts of synthetic hydrated silica are mixed well while being powdered to obtain a wettable powder.

FORMULATION EXAMPLE 4

Fifteen parts of Compound (I), 30 parts of haloxyfop-methyl, 3 parts of calcium ligninsulfonate, 2 parts of sodium laurylsulfate and 50 parts of synthetic hydrated silica are mixed well while being powdered to obtain a wettable powder.

FORMULATION EXAMPLE 5

Three parts of Compound (I), 60 parts of fenoxaprop-ethyl, 3 parts of calcium ligninsulfonate, 2 parts of sodium laurylsulfate and 32 parts of synthetic hydrated silica are mixed well while being powdered to obtain a wettable powder.

A composition comprising Compound (I) and Compound (II) thus formulated is useful for post-emergence control of undesired weeds by foliar treatment, for example. Further, in order to improve the herbicidal activity, the composition may be used together with other herbicides. Besides, it may be used in combination with insecticides, acaricides, nematocides, fungicides, plant growth regulators, etc. Due to the broad herbicidal spectrum, it may be also effective as the herbicide to be applied in plowed fields, non-plowed fields, borders for rice fields, orchards, pasture lands, lawns, forests, non-agricultural fields, etc.

The dosage of the active ingredients may vary depending on the mixing ratio, the formulation used, the crop and weed species, the prevailing weather conditions, the soil involved, etc. In general, however, the total amount of Compound (I) and Compound (II) is favored to be within a range of about 50 to 2000 grams per hectare. More specifically, the total amount of the active ingredients therein may be within a range of about 100 to 1000 grams per hectare.

In case of the composition being formulated into a wettable powder or a suspension, it is normally diluted with water and applied at a volume of about 100 to 1000 liters per hectare to the area where extermination of weeds is desired. The dilution may further contain, in addition to the above mentioned surface active agent, any spreading or auxiliary agent such as polyoxyethylene resin acid esters, ligninsulfonates, abietic acid, dinaphthylmethane-disulfonates, paraffin, petroleum oil and the like.

The practical herbicidal activity of the composition of the invention will be explained in further detail with reference to the following Test Examples wherein the growth controlling percentage (%) was determined by weighing the aerial parts of the test plants (fresh weight) and making calculation according to the following equation:

$$\text{Growth controlling percentage (\%)} = \left\{1 - \frac{\text{Fresh weight of test plant in treated plot}}{\text{Fresh weight of test plant in untreated plot}}\right\} \times 100$$

TEST EXAMPLE 1

Seeds of meadow foxtail were sowed in Wagner's pots (inner diameter, 16 cm; height, 19 cm) filled with upland field soil, and cultivated for 40 days outdoors. A designated amount of the composition in the form of a wettable powder formulated according to Formulation Example 1 was diluted with water containing a spreading agent and sprayed over the foliage of the test plants at a spray volume of 500 liters per hectare by the aid of a small hand sprayer. The spreading agent as used was a surfactant containing dialkylsulfosuccinate and added to water in an amount of 0.5% (v/v) in regard to the total dilution. At the time of the treatment, meadow foxtail had about 25 cm in height. The plants were cultivated outdoors for 21 days after the treatment, and the growth controlling percentage was observed. The results are shown in Tables 2 to 3.

TABLE 2

| Fluazifop-butyl (g/ha) | Growth controlling percentage of meadow foxtail (%) Compound (I) (g/ha) | | | | | | |
|---|---|---|---|---|---|---|---|
| | 0 | 6.3 | 12.5 | 25 | 50 | 100 | 400 | 800 |
| 0 | 0 | 0 | 3 | 9 | 19 | 32 | 81 | 94 |
| 50 | 14 | 24 | 47 | 58 | 67 | 85 | | |
| 100 | 31 | 41 | 64 | 80 | 89 | 93 | | |
| 200 | 49 | 71 | 87 | 97 | 100 | 100 | | |
| 400 | 79 | 96 | 100 | 100 | 100 | 100 | | |
| 800 | 91 | 100 | 100 | 100 | 100 | 100 | | |

TABLE 3

| Haloxyfop-methyl (g/ha) | Growth controlling percentage of meadow foxtail (%) Compound (I) (g/ha) | | | | | | |
|---|---|---|---|---|---|---|---|
| | 0 | 6.3 | 12.5 | 25 | 50 | 100 | 400 | 800 |
| 0 | 0 | 0 | 4 | 7 | 19 | 38 | 86 | 95 |
| 25 | 12 | 14 | 39 | 42 | 51 | 65 | | |
| 50 | 26 | 41 | 68 | 75 | 87 | 93 | | |
| 100 | 42 | 64 | 78 | 94 | 99 | 100 | | |
| 200 | 75 | 90 | 100 | 100 | 100 | 100 | | |
| 400 | 92 | 100 | 100 | 100 | 100 | 100 | | |

TEST EXAMPLE 2

Sandy plowed fields were turned up and, after border building, plotted into blocks of 3 m² each. Seeds of meadow foxtail, downy brome, catchweed bedstraw, persian speedwell and common chickweed were sowed therein, followed by cultivation for 130 days. The plants grown in heights of about 5 to 30 cm were treated with the test composition prepared in the same manner as in Test Example 1. The plants were cultivated for 21 days after the treatment, and the growth controlling activity was observed. The results are shown in Table 4.

TABLE 4

| Active ingredient | Dosage (g/ha) | Growth controlling percentage (%) | | | | |
|---|---|---|---|---|---|---|
| | | Meadow foxtail | Downy brome | Catchweed bedstraw | Persian speedwell | Common chickweed |
| Compound (I) | 30 | 6 | 3 | 82 | 96 | 92 |
| | 60 | 22 | 18 | 94 | 100 | 97 |
| | 360 | 70 | 52 | 100 | 100 | 100 |
| Fluazifop-butyl | 150 | 47 | 51 | 0 | 0 | 0 |
| | 300 | 78 | 81 | 0 | 0 | 0 |
| | 360 | 88 | 94 | 0 | 0 | 0 |
| Compound (I) + Fluazifop-butyl | 30 + 150 | 96 | 94 | 98 | 100 | 97 |
| | 60 + 150 | 100 | 100 | 100 | 100 | 100 |
| | 30 + 300 | 100 | 100 | 100 | 100 | 100 |
| | 60 + 300 | 100 | 100 | 100 | 100 | 100 |

TEST EXAMPLE 3

Winter wheats conventionally grown by stripe seeding cultivation in level row were harvested, and seeds of soybean were sowed between the wheat stubbles by drill seeding. Three days thereafter and before germination of soybean, a designated amount of the composition in the form of a wettable powder formulated according to Formulation Example 1 was diluted with water containing a spreading agent (80% of paraffin-based petroleum oil and 20% of polyoxyethylene sorbitan fatty acid ester and sorbitan fatty acid ester) in an amount of 1% (v/v) and sprayed uniformly over the top of the weeds remaining in the wheat field and having heights of about 20 to 50 cm by the aid of a small hand sprayer. After 40 days of the treatment, the growth controlling percentage on the weeds and the phytotoxicity to soybean were observed. The results are shown in Table 5 wherein the results with a mixture of glyphosate and metribuzin were also given for control.

TABLE 5

| Active ingredient | Dosage (g/ha) | Phyto- toxicity to soy- bean | Growth controlling percentage (%) | | | | |
|---|---|---|---|---|---|---|---|
| | | | Against weeds existed before treatment | | Against weeds germed after treatment | | |
| | | | Water fox- tail | Pale smart- weed | Barnyard grass | Slender amaranth | Pale smart- weed |
| Compound (I) + Fluazifop-butyl | 30 + 360 50 + 360 | 0 0 | 100 100 | 100 100 | 95 100 | 100 100 | 100 100 |
| Glyphosate + Metribuzin | 1000 + 400 | 3 | 100 | 100 | 87 | 100 | 100 |

The results in Test Example 1 were analyzed according to the isobole (i.e. equivalent efficacy line) method [Vol. 3, Herbicides, pages 109–111 (1981) in "Noyaku Jikkenho" (Methods in Pesticide Science) edited by Junichi Fukami et al., Soft Science Inc., Tokyo] based on the Tammes's method [Tammes, P. M. L.: Neth. J. Plant Path., 70, 73–80 (1964)]. Namely, several combinations of the compositions having different mixing ratios of Compound (I) and Compound (II) but exerting the same level of growth control effect, for example, 90% growth control, were plotted in a graph so as to readily determine a synergistic effect, an arithmetic effect or a competitive effect. In case of exhibiting the synergistic effect, the equivalent efficacy line as plotted is shown below the arithmetic efficacy line.

Figure 2:
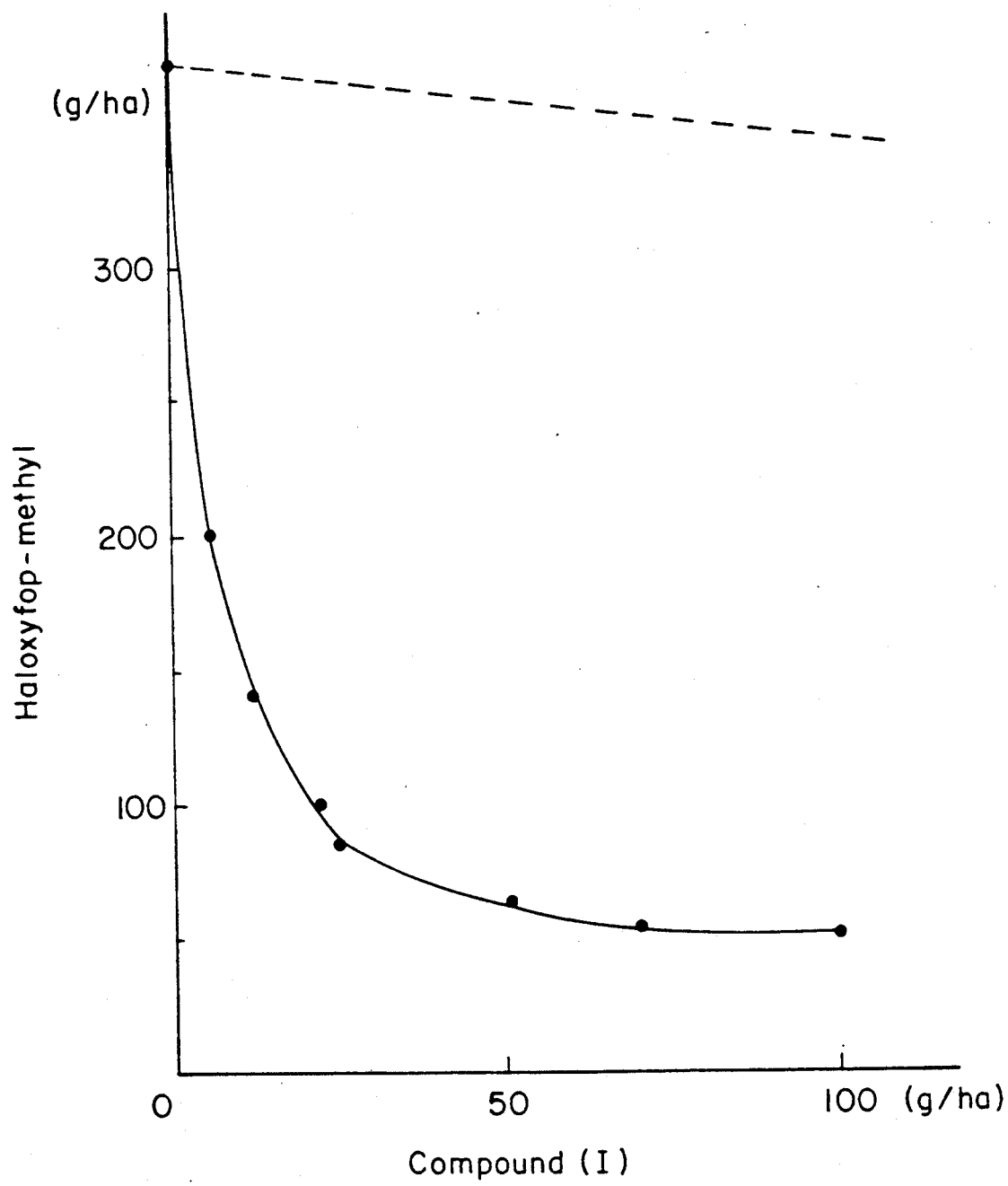

Explaining further in detail with reference to the accompanying drawings, FIG. 1 wherein the ordinate indicates the dosage of fluazifop-butyl and the abscissa indicates the dosage of Compound (I) show that the equivalent efficacy line (i.e. solid line) of 90% growth control of meadow foxtail is located below the arithmetic efficacy line (i.e. dotted line), from which it is understood that the associated use of Compound (I) and fluazifop-butyl in a certain mixing ratio produces a synergistic effect; and FIG. 2 wherein the ordinate indicates the dosage of haloxyfop-methyl and the abscissa indicates the dosage of Compound (I) shows that the equivalent efficacy line (i.e. solid line) of 90% growth control of meadow foxtail is located below the arithmetic efficacy line (i.e. dotted line), from which it is understood that the associated use of Compound (I) and haloxyfop-methyl in a certain mixing ratio produces a synergistic effect.

What is claimed is:

1. A herbicidal composition which comprises as an active ingredient a herbicidally effective amount of the combination (a) 2-{7-fluoro-3,4-dihydro-3-oxo-4-(2-propynyl)-2H-1,4-benzoxazin-6-yl}-4,5,6,7-tetrahydro-1H-isoindole-1,3(2H)-dione and (b) a compound of the formula:

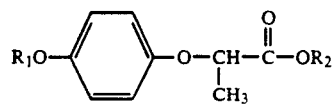

wherein $R_1$ is represented by the formula:

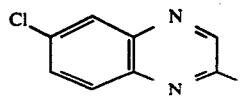

wherein $R_2$ is a $C_1$–$C_4$ alkyl group; and an inert carrier or diluent, wherein the weight proportion of the components (a) and (b) is from 1:0.4 to 1:20.

2. A method for controlling weeds which comprises applying a herbicidally effective amount of the composition according to claim 1 to the weeds in an amount of from 50 to 1000 grams per hectare.

* * * * *